(12) United States Patent
Ninomiya et al.

(10) Patent No.: US 11,167,148 B2
(45) Date of Patent: Nov. 9, 2021

(54) LIGHT EMITTING BONE IMPLANTS

(71) Applicant: Cimphoni Life Sciences LLC, Delafield, WI (US)

(72) Inventors: James T. Ninomiya, Brookfield, WI (US); Janine A. Struve, Milwaukee, WI (US); Dorothee Weihrauch, West Allis, WI (US); Scott Howard Micoley, Plymouth, WI (US); Dale Selsor DiIulio, Saukville, WI (US); Douglas J. Birkholz, Madison, WI (US); Kyle Steven Jansson, Brookfield, WI (US); Richard B. Davidson, Oconomowoc, WI (US)

(73) Assignee: CIMPHONI LIFE SCIENCES LLC, Delafield, WI (US)

( * ) Notice: Subject to any disclaimer, the term of this patent is extended or adjusted under 35 U.S.C. 154(b) by 882 days.

(21) Appl. No.: 15/444,114

(22) Filed: Feb. 27, 2017

(65) Prior Publication Data
US 2017/0245995 A1 Aug. 31, 2017

Related U.S. Application Data

(60) Provisional application No. 62/300,305, filed on Feb. 26, 2016, provisional application No. 62/373,842, filed on Aug. 11, 2016.

(51) Int. Cl.
*A61N 5/06* (2006.01)
*A61B 17/74* (2006.01)
(Continued)

(52) U.S. Cl.
CPC ........ *A61N 5/0601* (2013.01); *A61B 17/1668* (2013.01); *A61B 17/1721* (2013.01);
(Continued)

(58) Field of Classification Search
CPC ..... A61B 17/00; A61B 17/1725; A61B 17/17; A61B 8/00; A61B 17/7061; A61F 2/28;
(Continued)

(56) References Cited

U.S. PATENT DOCUMENTS

| 3,964,473 A | 6/1976 | Wickham |
| 4,026,304 A | 5/1977 | Levy |

(Continued)

FOREIGN PATENT DOCUMENTS

| CN | 1994235 A | 7/2007 |
| CN | 201029876 Y | 3/2008 |

(Continued)

OTHER PUBLICATIONS

International Search Report and Written Opinion for International Application No. PCT/US17/19756 dated Jun. 28, 2017, 11 pages.
(Continued)

*Primary Examiner* — Alvin J Stewart
(74) *Attorney, Agent, or Firm* — Quarles & Brady LLP

(57) ABSTRACT

A bone implant includes a bore extending entirely through the bone implant. The bone implant also includes a light source to emit light onto bone adjacent the bone implant to stimulate bone growth and/or reduce bone loss.

20 Claims, 11 Drawing Sheets

(51) Int. Cl.
*A61B 17/86* (2006.01)
*A61B 17/16* (2006.01)
*A61B 17/17* (2006.01)
*A61F 2/28* (2006.01)
*A61B 17/68* (2006.01)
*A61B 17/88* (2006.01)
*A61N 5/10* (2006.01)
*A61F 2/48* (2006.01)
*A61F 2/36* (2006.01)

(52) U.S. Cl.
CPC ........ *A61B 17/1742* (2013.01); *A61B 17/686* (2013.01); *A61B 17/742* (2013.01); *A61B 17/869* (2013.01); *A61B 17/8625* (2013.01); *A61B 17/88* (2013.01); *A61F 2/28* (2013.01); *A61N 5/0613* (2013.01); *A61N 5/1048* (2013.01); *A61B 17/86* (2013.01); *A61F 2/36* (2013.01); *A61F 2002/482* (2013.01); *A61N 2005/0612* (2013.01); *A61N 2005/0626* (2013.01); *A61N 2005/0651* (2013.01); *A61N 2005/0652* (2013.01); *A61N 2005/0653* (2013.01); *A61N 2005/0658* (2013.01); *A61N 2005/0659* (2013.01); *A61N 2005/0662* (2013.01); *A61N 2005/0663* (2013.01)

(58) Field of Classification Search
CPC . A61F 2/36; A61N 5/0601; A61N 2005/0612; A61N 5/0613; A61N 2005/0629; A61N 2005/063; A61N 2005/065; A61N 1/326; A61N 1/36
See application file for complete search history.

(56) References Cited

U.S. PATENT DOCUMENTS

| | | | |
|---|---|---|---|
| 4,313,438 A | 2/1982 | Greatbatch | |
| 4,314,554 A | 2/1982 | Greatbatch | |
| 4,549,547 A | 10/1985 | Brighton | |
| 4,602,638 A | 7/1986 | Adams | |
| 4,816,689 A | 3/1989 | Cavicchi | |
| 4,898,438 A | 2/1990 | Mori | |
| 4,898,439 A | 2/1990 | Mori | |
| 4,930,504 A | 6/1990 | Diamantopoulos | |
| 4,966,450 A | 10/1990 | Mori | |
| 4,978,186 A | 12/1990 | Mori | |
| 4,995,712 A | 2/1991 | Mori | |
| 5,030,236 A | 7/1991 | Dean | |
| 5,304,210 A | 4/1994 | Crook | |
| 5,330,477 A | 7/1994 | Crook | |
| 5,396,880 A | 3/1995 | Kagan | |
| 5,417,688 A | 5/1995 | Elstrom | |
| 5,441,527 A | 8/1995 | Erickson | |
| 5,445,608 A * | 8/1995 | Chen | A61N 5/0601 604/19 |
| 5,529,572 A | 6/1996 | Spector | |
| 5,540,691 A | 7/1996 | Elstrom | |
| 5,565,005 A | 10/1996 | Erickson | |
| 5,738,521 A | 4/1998 | Dugot | |
| 5,807,397 A | 9/1998 | Barreras | |
| 6,019,761 A | 2/2000 | Gustilo | |
| 6,063,108 A | 5/2000 | Salansky | |
| 6,120,502 A | 9/2000 | Michelson | |
| 6,143,035 A | 11/2000 | McDowell | |
| 6,270,492 B1 | 8/2001 | Sinofsky | |
| 6,290,714 B1 | 9/2001 | Streeter | |
| 6,471,716 B1 | 10/2002 | Pecukonis | |
| 6,503,269 B2 * | 1/2003 | Nield | A61B 18/22 607/89 |
| 6,537,304 B1 | 3/2003 | Oron | |
| 6,678,562 B1 | 1/2004 | Tepper | |
| 6,896,693 B2 | 5/2005 | Sullivan | |
| 7,455,672 B2 * | 11/2008 | Michelson | A61F 2/446 606/60 |
| 7,465,313 B2 * | 12/2008 | DiMauro | A61N 5/0601 128/898 |
| 7,513,906 B2 | 4/2009 | Passy | |
| 7,544,327 B2 | 6/2009 | Chung | |
| 7,814,916 B2 | 10/2010 | Revie | |
| 8,078,282 B2 | 12/2011 | Nycz | |
| 8,145,319 B1 | 3/2012 | Simon | |
| 8,206,387 B2 | 6/2012 | Michelson | |
| 8,244,368 B2 | 8/2012 | Sherman | |
| 8,249,696 B2 | 8/2012 | Fisher | |
| 8,262,713 B2 * | 9/2012 | Attawia | A61B 17/7001 606/328 |
| 8,267,883 B2 * | 9/2012 | DiMauro | A61L 31/146 604/8 |
| 8,366,711 B2 | 2/2013 | Rabiner | |
| 8,630,714 B1 | 1/2014 | Webb | |
| 8,725,262 B2 | 5/2014 | Olson | |
| 8,777,618 B2 | 7/2014 | Baehre | |
| 8,845,703 B2 | 9/2014 | Attawia | |
| 9,327,115 B2 | 5/2016 | Neuman | |
| 10,500,410 B2 * | 12/2019 | Ninomiya | A61B 17/869 |
| 2002/0087206 A1 * | 7/2002 | Hirschberg | A61N 5/0601 607/89 |
| 2003/0125782 A1 * | 7/2003 | Streeter | C12N 5/0656 607/88 |
| 2003/0225331 A1 | 12/2003 | Diederich | |
| 2004/0111132 A1 | 6/2004 | Shenderova | |
| 2004/0199219 A1 | 10/2004 | Dodge | |
| 2005/0096655 A1 | 5/2005 | Trinchese | |
| 2005/0175658 A1 * | 8/2005 | DiMauro | A61L 27/427 424/423 |
| 2006/0206209 A1 | 9/2006 | Cragg | |
| 2006/0265077 A1 | 11/2006 | Zwirkowski | |
| 2006/0271131 A1 * | 11/2006 | Passy | A61N 5/0613 607/88 |
| 2007/0073300 A1 * | 3/2007 | Attawia | A61B 17/86 606/328 |
| 2007/0100211 A1 * | 5/2007 | Selover | A61B 17/02 600/199 |
| 2007/0167998 A1 | 7/2007 | Loones | |
| 2007/0239232 A1 | 10/2007 | Kurtz | |
| 2007/0265682 A1 | 11/2007 | Wiegmann | |
| 2007/0270864 A1 * | 11/2007 | Gurtowski | A61B 5/0084 606/79 |
| 2008/0119421 A1 | 5/2008 | Tuszynski | |
| 2008/0125784 A1 * | 5/2008 | Rabiner | A61B 17/8836 606/92 |
| 2008/0154368 A1 | 6/2008 | Justis | |
| 2008/0154373 A1 | 6/2008 | Protopsaltis | |
| 2009/0062886 A1 | 3/2009 | O'Handley | |
| 2009/0143781 A1 | 6/2009 | Mische | |
| 2009/0177254 A1 | 7/2009 | Boyden | |
| 2010/0198316 A1 * | 8/2010 | Toselli | A61N 5/0601 607/88 |
| 2010/0317948 A1 * | 12/2010 | DiMauro | A61L 27/427 600/342 |
| 2010/0318161 A1 | 12/2010 | Brawn | |
| 2011/0118740 A1 | 5/2011 | Rabiner | |
| 2012/0029638 A1 | 2/2012 | Miller | |
| 2012/0041557 A1 | 2/2012 | Frigg | |
| 2012/0109304 A1 * | 5/2012 | Balckwell | A61B 17/7061 623/17.12 |
| 2012/0129131 A1 | 5/2012 | Baehre | |
| 2012/0185016 A1 | 7/2012 | Weiner | |
| 2012/0215281 A1 | 8/2012 | Neuman | |
| 2012/0232407 A1 * | 9/2012 | Fisher | A61B 17/7032 600/477 |
| 2012/0277812 A1 | 11/2012 | Kraus | |
| 2012/0310308 A1 | 12/2012 | Attawia | |
| 2013/0344560 A1 * | 12/2013 | Weston | C12N 13/00 435/173.8 |
| 2014/0088367 A1 | 3/2014 | DiMauro | |
| 2015/0148878 A1 | 5/2015 | Yoo | |
| 2016/0151639 A1 | 6/2016 | Scharf | |

(56) References Cited

U.S. PATENT DOCUMENTS

| | | | | |
|---|---|---|---|---|
| 2017/0231559 A1* | 8/2017 | Cuevas | ............... | A61B 5/4848 600/301 |
| 2017/0245995 A1* | 8/2017 | Ninomiya | .......... | A61B 17/1742 |
| 2017/0319867 A1 | 11/2017 | Ninomiya | | |

FOREIGN PATENT DOCUMENTS

| | | |
|---|---|---|
| DE | 3132488 A1 | 2/1983 |
| JP | 2007054468 A | 3/2007 |
| WO | WO 2003002201 A1 | 1/2003 |

OTHER PUBLICATIONS

International Search Report and Written Opinion for International Application No. PCT/US17/19759 dated Jul. 25, 2017, 11 pages.

\* cited by examiner

LIGHT EMITTING BONE IMPLANTS

RELATED APPLICATIONS

This application claims priority to U.S. Provisional Application No. 62/300,305, which is titled "Light Emitting Bone Implants" and was filed on Feb. 26, 2016. This application also claims priority to U.S. Provisional Application No. 62/373,842, which is titled "Light Emitting Bone Implants" and was filed on Aug. 11, 2016. Both U.S. Provisional Application No. 62/300,305 and U.S. Provisional Application No. 62/373,842 are incorporated by reference herein in their entireties.

BACKGROUND

Worldwide, osteoporosis may affect more than 200 million people and cause more than 8.9 million fractures annually, including about 1.6 million hip fractures. People who suffer a hip fracture often experience chronic pain, reduced mobility, disability, and an increased degree of dependence on other people. To reduce the risk of a hip fracture, medications are typically prescribed to treat osteoporosis. However, the efficacy of medications depends upon compliance, and studies have shown that only about 40 percent of patients take their medication for more than one year.

SUMMARY

In one embodiment of the invention, a bone implant includes an aperture extending entirely through the bone implant. The bone implant also includes a light source to emit light onto bone adjacent the bone implant to stimulate bone growth and/or reduce bone loss.

In another embodiment, a bone implant includes a rod having a longitudinal axis. The rod includes an aperture extending along the longitudinal axis and through the rod. The bone implant also includes a plurality of light sources coupled to the rod. The light sources are to emit light having wavelengths from about 600 nanometers to about 950 nanometers.

A method for surgically implanting a bone implant is provided by embodiments of the invention. The method includes positioning a guide wire along an axis passing through a bone and forming a bore in the bone along the axis based on a position of the guide wire. The method further includes positioning a bone implant so that the guide wire extends through an aperture of the bone implant. The bone implant includes a light source to emit light to stimulate bone growth and/or reduce bone loss. The method then includes inserting the bone implant into the bore.

DETAILED DESCRIPTION

Figure 1:
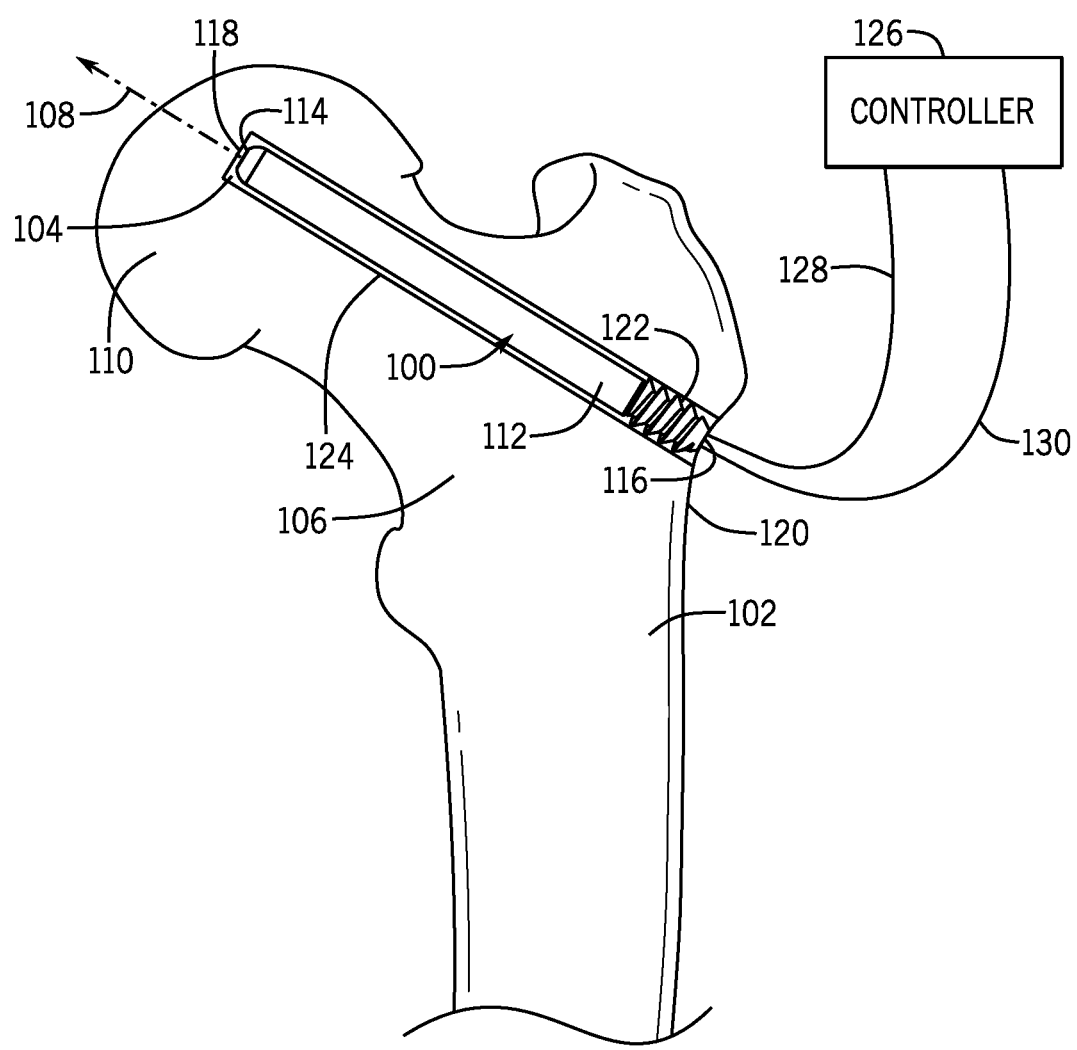
FIG. 1 is a schematic illustration of a bone implant positioned in a femur of a patient according to one embodiment of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

The light emitting bone implants in some embodiments of the invention deliver predetermined doses of light to bone to stimulate bone growth and/or reduce bone loss. For example, a light emitting bone implant can be implanted into a bore drilled in a femur of a patient. The bone implant includes one or more light sources, such as organic light emitting diodes that emit near infrared (NIR) light (e.g., light having wavelengths from about 600 nanometers to about 950 nanometers). In some embodiments, the light penetrates the bone by about one-sixteenth of an inch, decreasing osteoblast apoptosis and promoting cell proliferation of the bone. For example, after 15 weeks of treatment to an ovariectomized (OVX) bone via the light emitting bone implants disclosed herein, bone mass of the OVX bone may increase by 2.5 times to 3 times relative to an OVX bone that receives no treatment.

In some embodiments, the light sources of the bone implant are operatively coupled to a controller, and the controller controls dosages (e.g., a duration of exposure at a predetermined irradiance level) and/or frequencies (e.g., duty cycle or time between exposures) at which light sources deliver doses of light to the patient. For example, in some embodiments, the controller supplies power to the bone implant and, thus, the light sources, for a predetermined amount of time (e.g., thirty to sixty seconds) at predetermined times (e.g., once per day at noon, every twelve hours, etc.) to control an amount of light delivered to the patient. In some embodiments, the controller controls power to the bone implant and, thus, the light sources so that the bone implant delivers about three to thirty Joules of energy per day via light emitted by the light sources. In some embodiments, the controller controls an amount of heat generated via the light emitting bone implant to prevent the light emitting bone implant from generating an amount of heat that damages or kills osteoblasts.

The controller can be implanted in the patient. In some embodiments, the controller includes a rechargeable power source such as a battery. Thus, the battery may be implanted in the patient. In one embodiment, the power source may be recharged via inductive charging. For example, the patient may employ a handheld device that generates an alternating magnetic field that the patient positions in proximity to the power source (e.g., the patient may press the handheld device against his or her skin near the power source). In some embodiments, the power source includes an induction coil that converts the alternating electromagnetic field to electric current that recharges the power source.

FIG. 1 illustrates a bone implant 100 according to one embodiment of the invention. The bone implant 100 is surgically implanted into a femur 102 of a patient. Although the following description involves the femur 102, the bone implants disclosed herein may be implanted into other bones to stimulate bone growth and/or reduce bone loss. A bore 104 is drilled into a neck 106 of the femur 102 along an axis 108 extending through a center of a head 110 of the femur 102. The bone implant 100 is inserted into the bore 104 and secured to the femur 102.

The bone implant 100 includes a rod 112 disposed entirely within the bore 104. The rod 112 includes a first or fore end 114 and a second or aft end 116. The first end 114 is disposed adjacent an end wall 118 of the bore 104. In some embodiments, the second end 116 is flush with an outer cortex 120 of the femur 102. When the second end 116 is flush with the outer cortex 120, the first end 114 is at a depth of the bore 104 substantially equal to a length of the rod 112. In other embodiments, the second end 116 is recessed relative to the outer cortex 120. When the second end 116 is recessed relative to the outer cortex 120, the first end 114 is at a depth of the bore 104 deeper than the length of the rod 112.

The rod 112 includes male threads 122 at and/or near the second end 116 of the rod 112. The male threads 122 engage a portion of a sidewall 124 of the bore 104 adjacent the outer cortex 120 to secure the rod 112 to the femur 102 and cantilever the rod 112 within the bore 104. For example, the rod 112 of FIG. 1 is secured to the bore 104 so that the first end 114 is spaced apart from and, thus, not in contact with the sidewall 124 of the bore 104. As described in greater detail below, the bone implant 100 emits light into the bore 104 to expose the femur 102 to the light to stimulate bone growth and/or reduce bone loss.

A controller 126 is operatively coupled to the bone implant 100. The controller 126 controls a dosage of light delivered by the bone implant 100 and a frequency and/or schedule at which the bone implant 100 delivers a dose of the light. The controller 126 is dimensioned to be implantable in the patient. For example, the controller 126 can be dimensioned to be about a size of a computer mouse. In some embodiments, the controller 126 is implanted in subcutaneous tissue of the patient. In some embodiments, the controller 126 is operatively coupled to the bone implant 100 via a first lead 128 and a second lead 130. The first lead 128 and the second lead 130 may extend through a subcutaneous tunnel (not shown) to electrically connect the first lead 128 and the second lead 130 to the bone implant 100. In other embodiments, the bone implant 100 is operatively coupled to the controller 126 in one or more additional and/or alternative ways such as wirelessly via a wireless communications link.

Figure 1A:
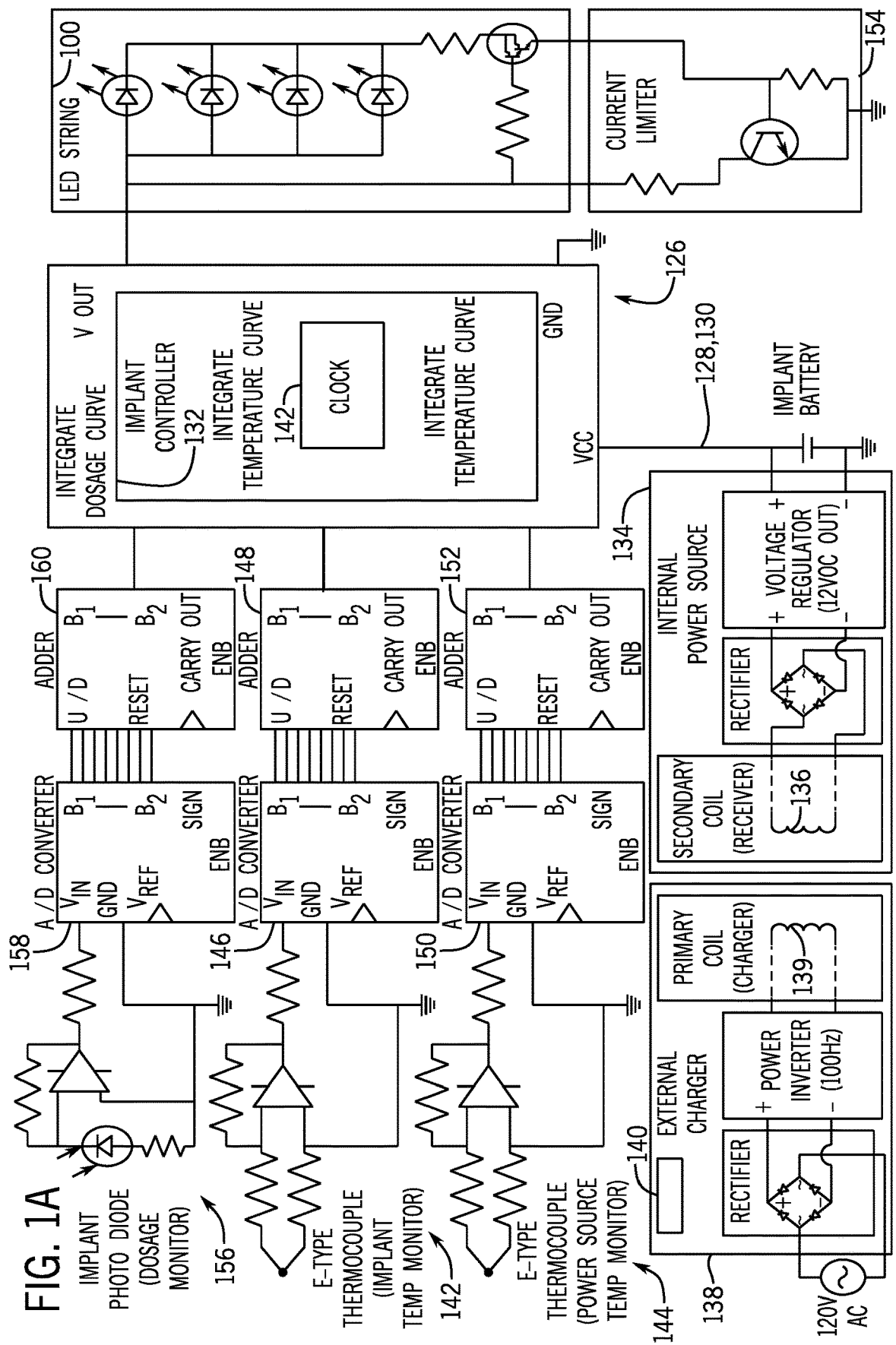
FIG. 1A is a schematic illustration of a controller operatively coupled to the bone implant of FIG. 1.

FIG. 1A is a schematic illustration of the controller 126 of FIG. 1. The controller 126 includes a processor 132 (e.g., a microprocessor) and a power source 134. The power source 134 supplies power to the bone implant 100 via the first lead 128 and the second lead 130. In some embodiments, the power source 134 includes one or more rechargeable batteries such as, for example, a DC battery (e.g., lithium/silver vanadium oxide battery). In some embodiments, the one or more batteries has a capacity of about 1500 milliamp-hours to about 2000 milliamp-hours. The one or more rechargeable batteries may be housed in an inert housing (not shown). For example, the housing can be constructed of 316L stainless steel, titanium, cobalt chrome, molybdenum alloy, and/or one or more additional and/or alternative materials. In some embodiments, the power source 134 includes a first induction coil 136 to enable the power source 134 to be recharged via inductive charging. For example, the patient may employ a handheld device 138 that generates an alternating electromagnetic field via a second induction coil 139. When the patient positions the handheld device 138 in proximity of the power source 134, the first induction coil 136 of the power source 134 converts the alternating electromagnetic field to electric current. In some embodiments, the handheld device 138 includes an output device 140 (e.g., a light, a speaker, etc.) to indicate that the handheld device 138 is positioned in proximity of the power source 134 to charge the power source 134. For example, if the handheld device 138 is positioned within about one inch of the power source 134, the handheld device 138 can illuminate a light on the handheld device 138 and/or generate a noise such as a beep to indicate that the handheld device 138 is positioned in proximity of the power source 134 to charge the power source 134.

In some embodiments, the controller 126 includes a first thermocouple 142 and a second thermocouple 144 (e.g., type E thermocouples) to determine an amount of heat generated by the bone implant 100 (e.g., during exposure of bone to light) and the power source 134 (during discharge or recharge), respectively. In some such embodiments, the controller 126 prevents the power source 134 from supplying power to the bone implant 100 if the controller 126 determines that the bone implant 100, the controller 126 and/or the power source 134 exceeds a predetermined temperature (e.g., 38.5° C.). For example, in the illustrated embodiment, the first thermocouple 142 includes a first analog-to-digital converter (ADC) 146 and a first adder 148. The first thermocouple 142 feeds a thermo-electric voltage from to the first ADC 146, and the first ADC 146 converts the voltage to a digital signal. The first adder 148 and an integrator of the processor 132 collect and integrate a change in temperature over time to determine if the predetermined temperature of the bone implant 100 has been exceeded. If the temperature of the bone implant 100 has exceeded the predetermined temperature, the controller 126 discontinues operation of the bone implant 100 (e.g., stops supplying power to the bone implant 100).

In the illustrated embodiment, the second thermocouple 144 includes a second analog-to-digital converter (ADC) 150 and a second adder 152. The second thermocouple 144 feeds a thermo-electric voltage to the second ADC 150, and the second ADC 150 converts the voltage to a digital signal. The second adder 152 and an integrator of the processor 132 collect and integrate a change in temperature over time to determine if the predetermined temperature of the power source 134 has been exceeded. If the temperature of the power source 134 has exceeded the predetermined temperature, the controller 126 discontinuous operation of the power source 134 (e.g., stops recharging the power source 134).

In some embodiments, a current limiter and/or a shunt failsafe 154 is operatively coupled to the controller 126 to prevent the power source 134 from supplying current to the bone implant 100 if the controller 126 does not properly operate the bone implant 100 and/or if the power source 134 exceeds a predetermined rate of current flow during discharge or recharge of the power source 134 (e.g., 100 milliamps over sixty seconds, 500 milliamps over ten seconds, and/or any other predetermined rate).

In some embodiments, the processor 132 includes a clock 142 that determines and/or monitors, for example, a time of day, a day of week, etc. The processor 132 controls times at which the power source 134 supplies power to the bone implant 100 and/or durations of time that the power source 134 supplies power to the bone implant 100 based on the clock 142. The durations of time that the power source 134 supplies power to the bone implant 100 control dosages of light delivered by the bone implant 100. For example, in some embodiments, the processor 132 controls the power source 134 so that the power source 134 supplies power to the bone implant 100 for about thirty to sixty seconds per day to enable the bone implant 100 to deliver a total of four to six Joules of energy per day. For example, the processor 132 may control the power source 134 such that the bone implant 100 delivers a single dose of four to six Joules of energy per day. In other embodiments, the processor 132 controls the power source 134 such that the bone implant 100 delivers more than one dose per day that sum to four to six Joules of energy per day (e.g., five to ten second doses every four hours). In other embodiments, the processor 132 controls the power source 134 to enable the bone implant 100 to deliver different dosages of light or energy (e.g., one Joule, five Joules, ten Joules, etc.) each day and/or at other frequencies (e.g., twice per day, three times per day, continuously, etc.).

In some embodiments, the controller 126 controls a dosage of light delivered via the bone implant 100 based on an amount of light emitted via the bone implant 100. For example, the controller 126 and/or the bone implant 100 can include a photodiode 156 that receives light emitted via the bone implant 100 and communicates a signal to the controller 126 indicative of an amount of light received by the photodiode. In some embodiments, the photodiode 156 is disposed on the bone implant 100 and receives light reflected from the femur 102. The photodiode 156 includes a third ADC converter 158 and a third adder 160. The photodiode 156 converts light into an analog current signal and feeds the analog current signal to a negative terminal of an Operational Amplifier. The Operational Amplifier amplifies the analog current signal and converts the analog current signal into a voltage. The third ADC 158 converts the voltage into a digital signal, and the third adder 160 and the processor 132 sum the digital signal over a period of time during which the bone implant 100 emits light. When the sum reaches a predetermined value corresponding to a dose of light (e.g., four to six Joules of energy), the controller 126 disconnects the power source 134 from the bone implant 100 and resets the third adder 160 to zero.

Figure 2:
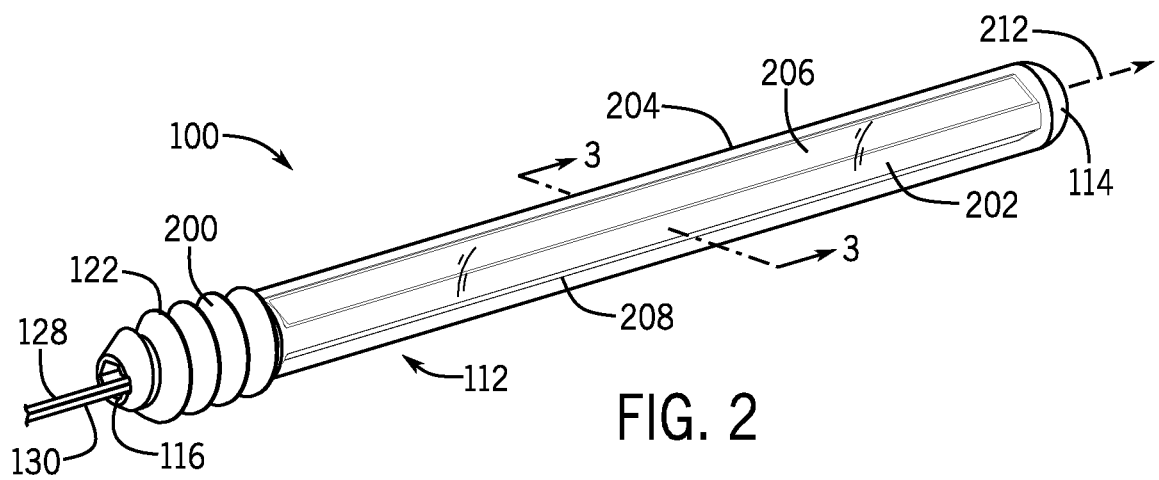
FIG. 2 is a perspective view of the bone implant of FIG. 1.
Figure 3:
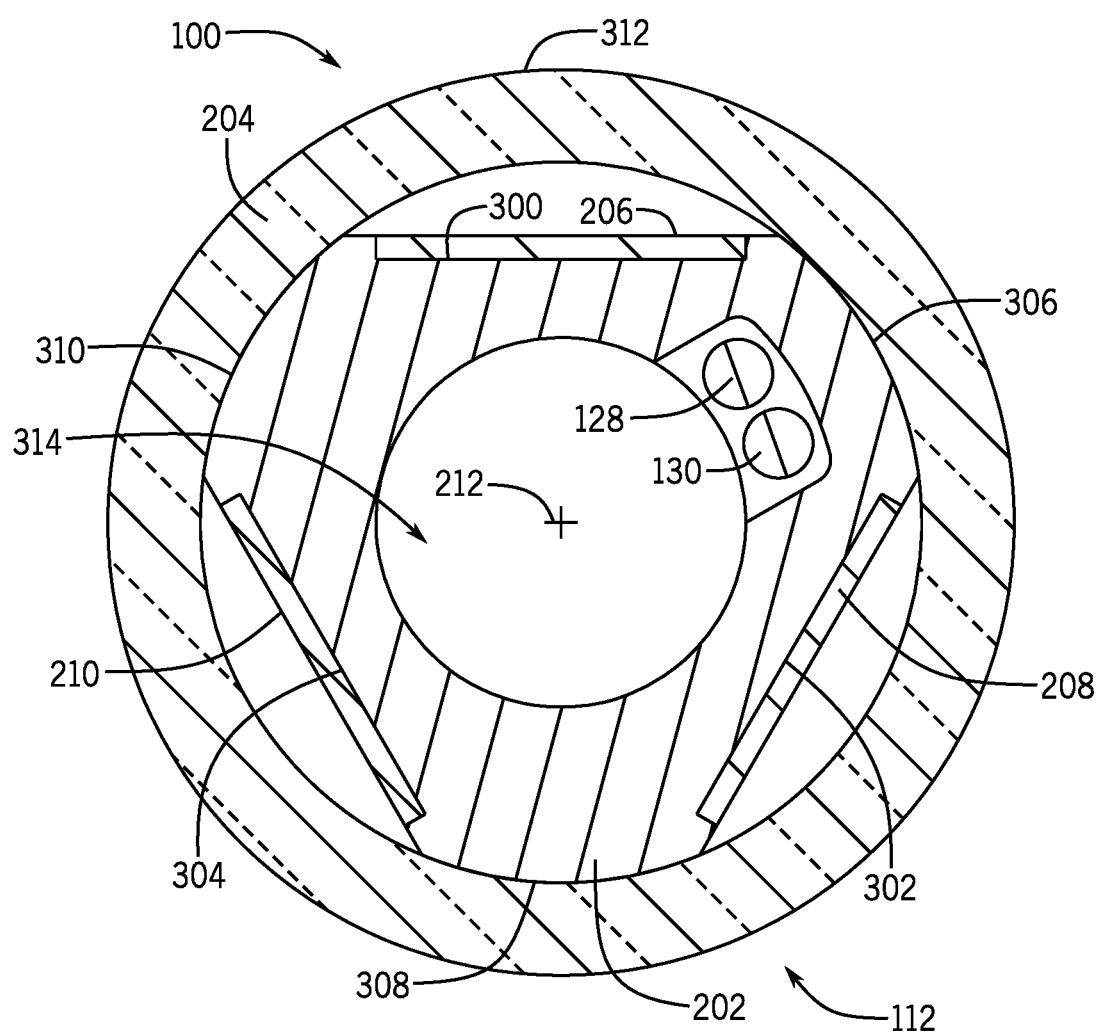
FIG. 3 is a cross-sectional view of the bone implant of FIGS. 1-2 along line 3-3 of FIG. 2.

FIG. 2 is a perspective view of the bone implant 100 of FIG. 1. The rod 112 of the bone implant 100 includes a head 200, a base 202, and a cover 204. In some embodiments, the head 200 and the base 202 are constructed of one or more inert materials such as, for example, 316L stainless steel, titanium, cobalt chrome, molybdenum alloy, etc. The head 200 includes the threads 122 that engage the sidewall 124 of the bore 104. The base 202 extends from the head 200. In the embodiment of FIG. 2, a first light source 206, a second light source 208, and a third light source 210 (as shown in FIG. 3) are coupled to the base 202. For example, the first light source 206, the second light source 208, and the third light source 210 can be coupled to the base 202 via a conductive adhesive such as paste or glue. In some embodiments, the first light source 206, the second light source 208, and the third light source 210 are in contact with the base 202 to facilitate heat transfer from the first light source 206, the second light source 208, and the third light source 210 to the base 202. Thus, the base 202 can be a heat sink.

In the illustrated embodiment, the first light source 206, the second light source 208, and the third light source 210 are daisy chained (i.e., connected together in series) and operatively coupled to the controller 126 via the leads 128, 130. In some embodiments, the first light source 206, the second light source 208, and the third light source 210 are strips of light emitting diodes ("LED strips"). In some embodiments, the LED strips are organic LED strips. In some embodiments, the LED strips are thin, flexible strips having light emitting diodes connected in parallel. In some embodiments, each of the LED strips generates radiant power exposure of about 200 to about 250 milliwatts per square centimeter (mw/cm$^2$). In some embodiments, the LED strips each have a thickness of about two to three millimeters, a width of about six to ten millimeters, and a length substantially equal to a length of the rod 112 (e.g., 80-100 millimeters). However, the above-noted dimensions are merely examples and, thus, other dimensions may be used without departing from the scope of this disclosure. In some embodiments, each of the LED strips has a viewing angle of about 120 degrees to about 170 degrees. In other embodiments, the first light source 206, the second light source 208, and the third light source 210 are implemented in one or more additional and/or alternative ways. In some embodiments, the first light source 206, the second light source 208, and the third light source 210 deliver light to substantially all portions of the sidewall 124 of the bore 104 deeper than the head 200 of the rod 112. In some embodiments, the first light source 206, the second light source 208, and the third light source 210 deliver light to the end wall 118 of the bore 104.

In some embodiments, the first light source 206, the second light source 208, and the third light source 210 emit near infrared (NIR) light (e.g., light having wavelengths from about 600 nanometers to about 950 nanometers). In some embodiments, the first light source 206, the second light source 208, and the third light source 210 emit light having wavelengths of about 670 nanometers. In some embodiments, the light penetrates the femur 102 by about one-sixteenth of an inch, decreasing osteoblast apoptosis and promoting cell proliferation of the femur 102. Although the bone implant 100 of FIG. 2 has three light sources, the bone implant 100 can include other numbers of light sources in other embodiments. For example, the bone implant 100 can include one light source, two light sources, five light sources, or other suitable numbers of individual or groups of light sources.

In some embodiments, the rod 112, the first light source 206, the second light source 208, and the third light source 210 extend substantially parallel to a central, longitudinal axis 212 of the rod 112. In other embodiments, the first light source 206, the second light source 208, and the third light source 210 are oriented in other ways. For example, the first light source 206, the second light source 208, and/or the third light source 210 can wrap around the base 202 substantially perpendicularly to the central, longitudinal axis 212 of the rod 112. In some embodiments, the first light source 206, the second light source 208, and/or the third light source 210 spiral around the base 202 (e.g., helically).

In some embodiments, the cover 204 covers the base 202 and the first light source 206, the second light source 208, and the third light source 210. In some embodiments, the cover 204 prevents the first light source 206, the second light source 208, and the third light source 210 from contacting bodily fluids during and after implantation of the bone implant 100. In one embodiment, the cover 204 is transparent or clear. In other embodiments, the cover 204 is translucent. In one embodiment, the cover 204 is poly(methyl methacrylate) ("PMMA") overmolded to the base 202 and/or the first light source 206, the second light source 208, and the third light source 210. In some embodiments, the cover 204 is a sleeve or tube, and the base 202 and the first light source 206, the second light source 208, and the third light source 210 are received in a receptacle of the sleeve.

FIG. 3 is a cross-sectional view of the bone implant 100 of FIGS. 1-2 taken along line 3-3 of FIG. 2, which is perpendicular to the central, longitudinal axis 212 of the rod 112. In one embodiment, the base 202 has a trilobate cross-sectional shape. For example, the base 202 includes a first planar side 300, a second planar side 302, and a third planar side 304 disposed equidistantly (e.g., about 120 degrees apart) about the central, longitudinal axis 212 of the rod 112. A first curved surface 306 extends from the first planar side 300 to the second planar side 302. A second curved surface 308 extends from the second planar side 302 to the third planar side 304. A third curved surface 310 extends from the third planar side 304 to the first planar side 300. Thus, the base 202 has a cross-sectional shape of an equilateral triangular with rounded corners. In other embodiments, the base 202 has other cross-sectional shapes such as rectangular, circular, elliptical, etc.

In the illustrated embodiment, the first light source 206, the second light source 208, and the third light source 210 are seated on the first planar side 300, the second planar side 302, and the third planar side 304, respectively. The cover 204 surrounds the base 202 and the first light source 206, the second light source 208, and the third light source 210. In the illustrated embodiment, an exterior surface 312 of the cover 204 is cylindrical. In other embodiments, the exterior surface 312 of the cover 204 is other shapes such as rectangular, circular, elliptical, etc.

The first light source 206, the second light source 208, and the third light source 210 deliver light through the cover 204 to substantially all portions of the sidewall 124 of the bore 104 deeper than the head 200 of the rod 112. In some embodiments, the rod 112 includes a bore or aperture 314 that extends entirely through the bone implant 100 along the central, longitudinal axis 212. Thus, the aperture 314 provides a continuous passage from the first end 114 to the second end 116 of the rod 112. As a result, the aperture 314 enables the rod 112 to be inserted into the bore 104 of the femur 102 via a guide wire. For example, a surgeon can employ a guide wire to drill or ream the bore 104 to a predetermined depth along the axis 108 extending through the center of a head 110 of the femur 102. Once the bore 104 is drilled or reamed, the surgeon inserts the guide wire into the aperture 314 of the rod 112 to direct the rod 112 into the bore 104 of the femur 102 via a path of the guide wire.

Figure 4:
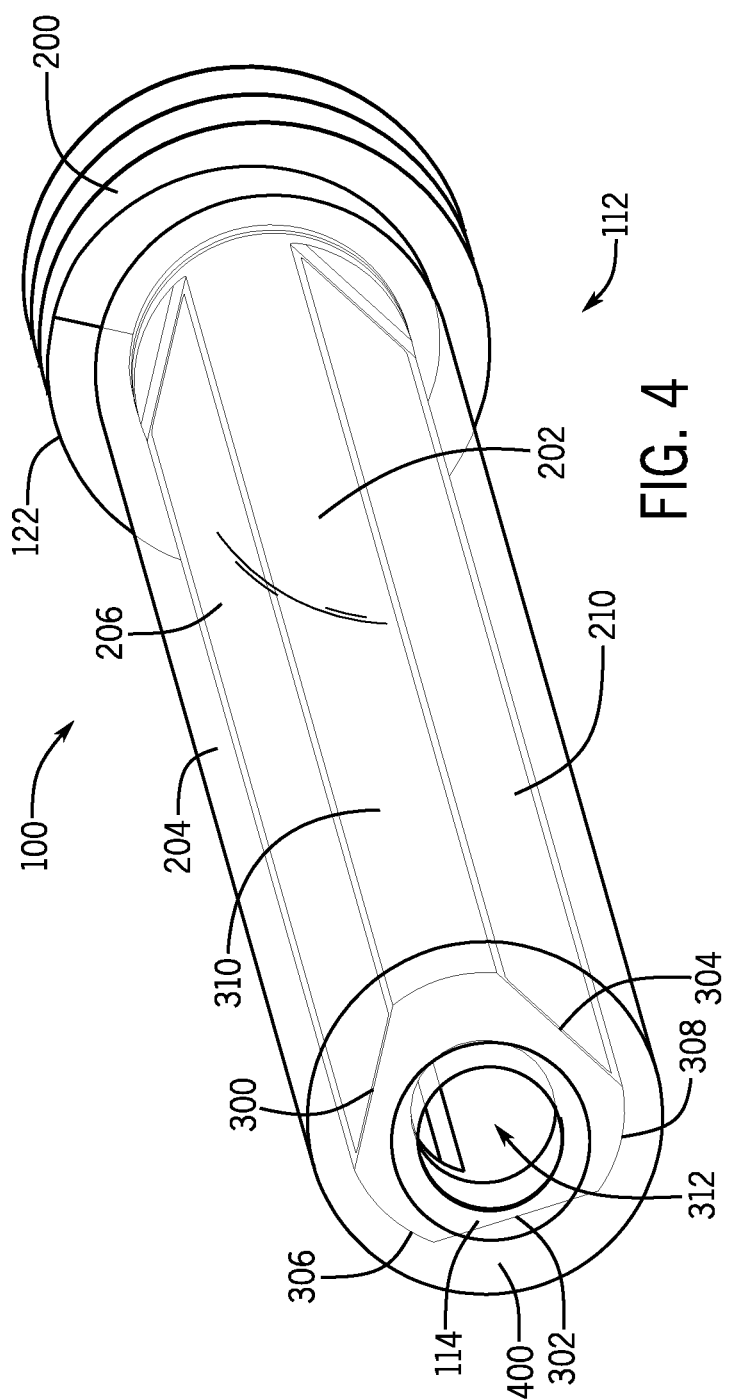
FIG. 4 is another perspective view of the bone implant of FIGS. 1-3.

FIG. 4 is a perspective view of the bone implant 100 of FIGS. 1-4. The cover 204 includes a cap 400 defining the first end 114 of the rod 112. The cap 400 is transparent or clear. As a result, light emitted from the first light source 206, the second light source 208, and/or the third light source 210 (as shown in FIG. 3) travels through the first end 114 of the rod 112 to deliver light to the end wall 118 of the bore 104. In some embodiments, the cap 400 is translucent.

Figure 5:
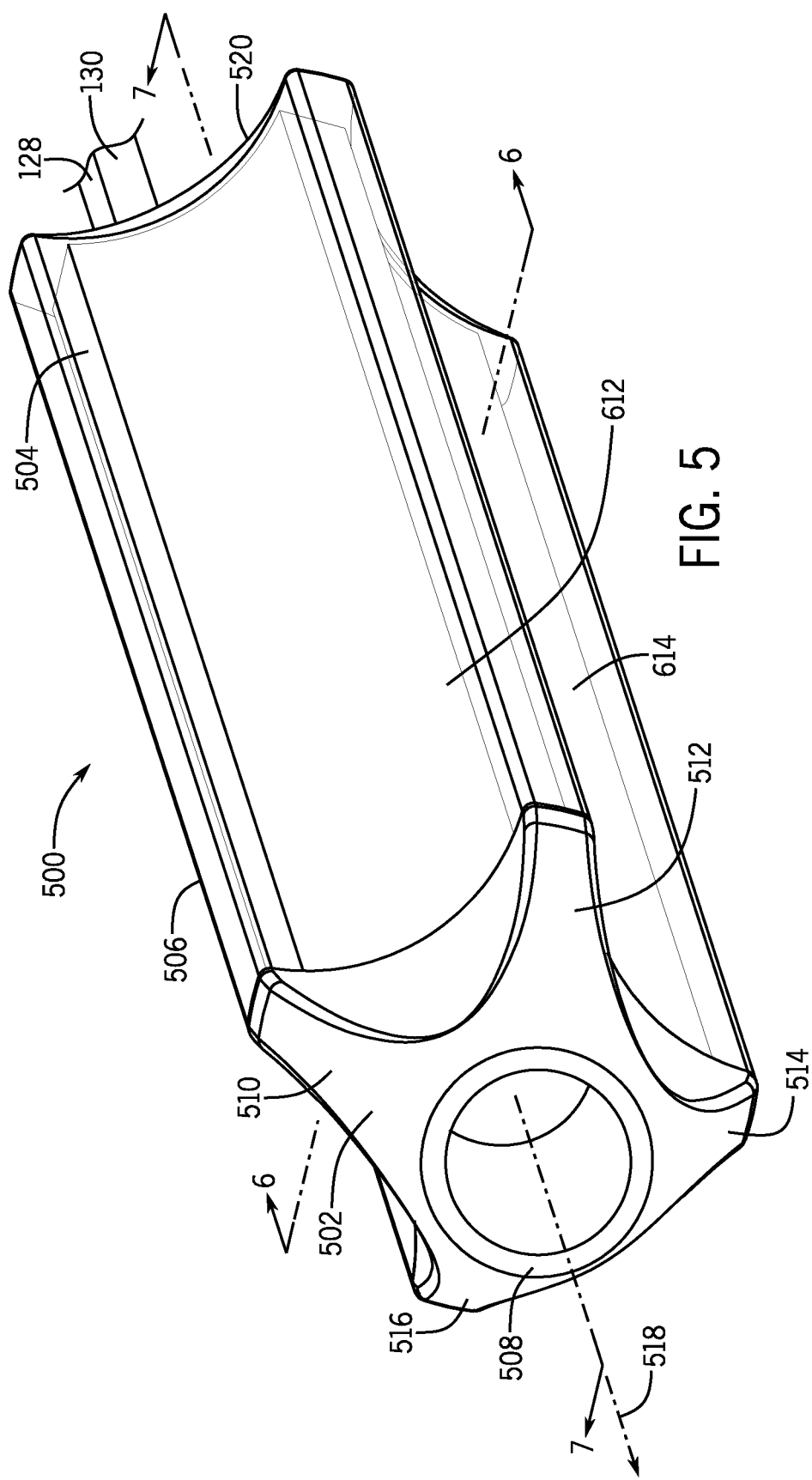
FIG. 5 is a perspective view of a bone implant according to another embodiment of the invention.

FIG. 5 is a perspective view of another embodiment of a bone implant 500 disclosed herein, which may be received in the bore 104 of the femur 102 of FIG. 1 and operatively coupled to the controller 126 via the first lead 128 and the second lead 130. The bone implant 500 includes a head 502, a base 504, and a cover 506. In some embodiments, the head 502 and the base 504 are one or more inert materials such as, for example, 316L stainless steel, titanium, cobalt chrome, molybdenum alloy, and/or one or more additional and/or alternative materials. The head 502 of FIG. 5 can taper toward a first end 508 of the bone implant 500. In some embodiments, the first end 508 is pointed and/or sharp to enable the head 502 to pierce the end wall 118 of the bore 104 to secure the bone implant 500 to the femur 102.

The bone implant 500 includes a first spline 510, a second spline 512, a third spline 514, and a fourth spline 516 (collectively "the splines 510, 512, 514, 516"). In some embodiments, the first spline 510, the second spline 512, the third spline 514, and the fourth spline 516 can have sharp edges to cut grooves into the femur 102 as the bone implant 500 is implanted into the bore 104 of the femur 102. In one embodiment, the first spline 510, the second spline 512, the third spline 514, and the fourth spline 516 are disposed equidistantly (e.g., about 90 degrees apart) about a central, longitudinal axis 518 of the bone implant 500 and extend substantially parallel to the central, longitudinal axis 518 of the bone implant 500. Thus, the first spline 510 is opposite the third spline 514, and the second spline 512 is opposite the fourth spline 516. In one embodiment, the splines 510, 512, 514, 516 extend from the first end 508 of the bone implant 500 to a second end 520 of the bone implant 500 opposite the first end 508. As described below with reference to FIG. 6, light sources 612, 614, 616, 618 are disposed on the bone implant 500 between the splines 510, 512, 514, 516, respectively.

In some embodiments, when the bone implant 500 is implanted in the femur 102, the bone implant 500 is disposed entirely within the bore 104. For example, when the bone implant 500 is disposed in the bore 104, the first end 508 pierces the end wall 118 of the bore 104. In some embodiments, the second end 520 is flush with the outer cortex 120 of the femur 102. In other embodiments, the second end 520 is recessed relative to the outer cortex 120.

Figure 6:
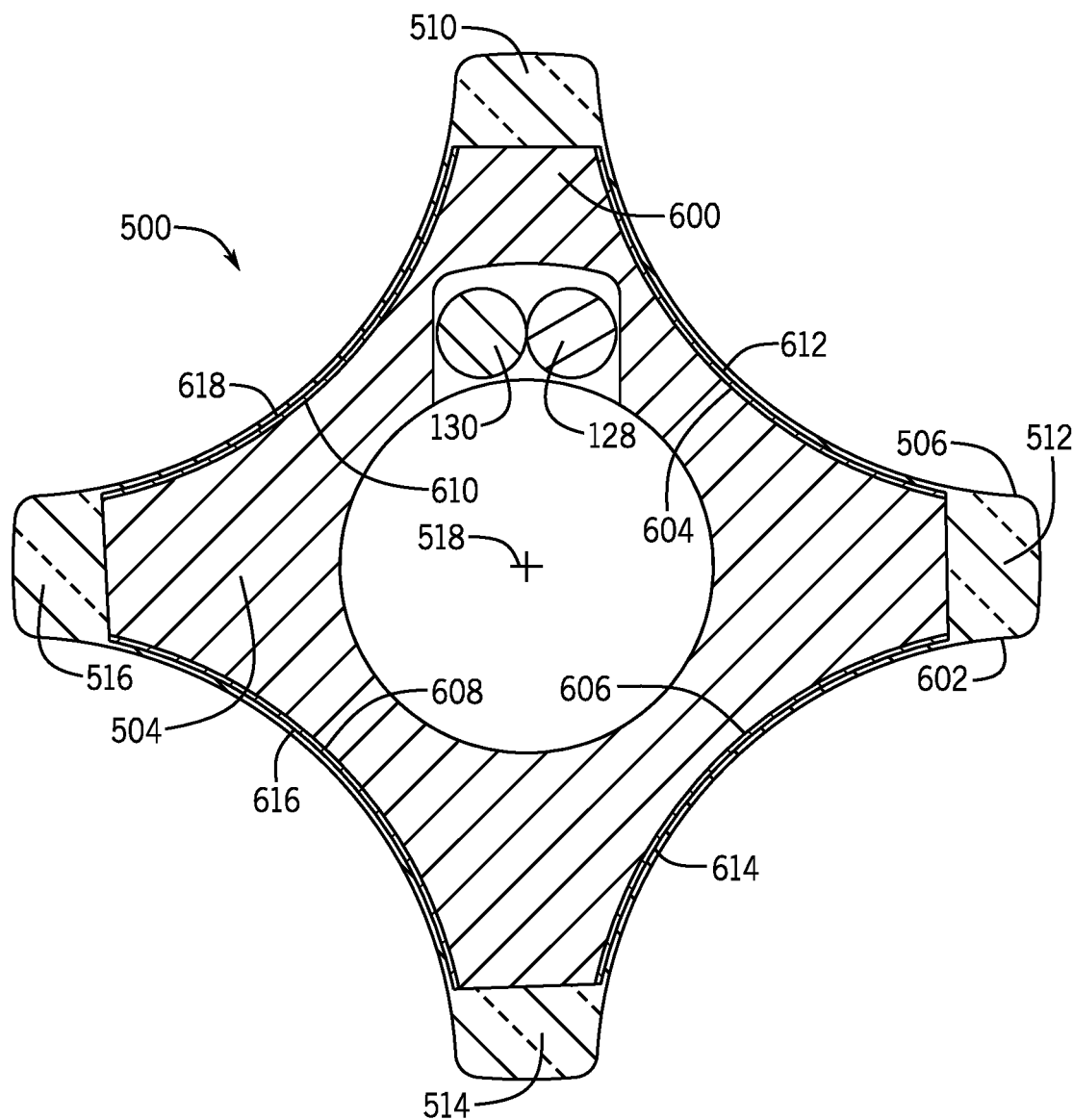
FIG. 6 is a cross-sectional view of the bone implant of FIG. 5 along line 6-6 of FIG. 5.

FIG. 6 is a cross-sectional view of the bone implant 500 of FIG. 5 along line 6-6 of FIG. 5. In some embodiments, the base 504 and the cover 506 cooperate to define the splines 510, 512, 514, 516. For example, the base 504 includes a core 600 of the splines 510, 512, 514, 516, and the cover 506 surrounds the core 600 and defines exterior surfaces 602 of the splines 510, 512, 514, 516.

In some embodiments, the base 504 includes a first flute 604, a second flute 606, a third flute 608, and a fourth flute 610. The first flute 604 is a concave surface between the first spline 510 and the second spline 512. The second flute 606 is a concave surface between the second spline 512 and the third spline 514. The third flute 608 is a concave surface between the third spline 514 and the fourth spline 516. The fourth flute 610 is a concave surface between the fourth spline 516 and the first spline 510. In other embodiments, the first flute 604, the second flute 606, the third flute 608, and/or the fourth flute 610 have other shapes and/or contours. For example, the first flute 604, the second flute 06, the third flute 608, and/or the fourth flute 610 can be planar, stepped, convex, etc.

In one embodiment, the bone implant 500 includes a first light source 612, a second light source 614, a third light source 616, and a fourth light source 618 (collectively "the light sources 612, 614, 616, 618"). The first light source 612, the second light source 614, the third light source 616, and the fourth light source 618 are operatively coupled to the controller 126. The first light source 612 is disposed on the first flute 604; the second light source 614 is disposed on the second flute 606; the third light source 616 is disposed on the third flute 608; and the fourth light source 618 is disposed on the fourth flute 610. In some embodiments, the light sources 612, 614, 616, 618 are coupled to the base 504 via a conductive adhesive such as paste or glue. In some embodiments, the light sources 612, 614, 616, 618 are in contact with the base 504 to facilitate heat transfer from the light sources 612, 614, 616, 618 to the base 504. Thus, the base 504 can be a heat sink. In one embodiment, each of the light sources 612, 614, 616, 618 is an LED strip extending substantially parallel to the central, longitudinal axis 518 of the bone implant 500. In other embodiments, the light sources 612, 614, 616, 618 are implemented in other ways. In some embodiments, each of the LED strips generates radiant power exposure of about 200 to about 250 mw/cm$^2$. In some embodiments, the LED strips are organic LED strips. In some embodiments, the LED strips are thin, flexible strips having light emitting diodes connected in parallel. In some embodiments, the LED strips each have a thickness of about two to three millimeters, a width of about six to ten millimeters, and a length substantially equal to a length of the base 504 (e.g., 80-100 millimeters). However, the above-noted dimensions are merely examples and, thus, other dimensions may be used without departing from the scope of this disclosure.

In some embodiments, the light sources 612, 614, 616, 618 emit near infrared (NIR) light (e.g., light having wavelengths from about 600 nanometers to about 950 nanometers). In some embodiments, the light sources 612, 614, 616, 618 emit light having wavelengths of about 670 nanometers. In some embodiments, the light penetrates the femur 102 by about one-sixteenth of an inch, decreasing osteoblast apoptosis and promoting cell proliferation of the femur 102. In some embodiments, each of the light sources 612, 614, 616, 618 has a viewing angle of about 120 degrees to about 170 degrees. In other embodiments, one or more of the light sources 612, 614, 616, 618 has other viewing angles. In some embodiments, each of the light sources 612, 614, 616, 618 has a light coverage of about 100 percent at a distance of about 2 to 3 millimeters outward (i.e., perpendicular to the central, longitudinal axis 518) from the respective one of the light sources 612, 614, 616, 618. Although the bone implant 500 of FIGS. 5-6 has four light sources, the bone implant 500 can include other numbers of light sources in other embodiments. For example, the bone implant 500 may include one light source, two light sources, five light sources, or other suitable numbers of individual or groups of light sources.

In some embodiments, the cover 506 is PMMA overmolded to the base 504 and the light sources 612, 614, 616, 618. In some embodiments, the cover 506 is a sleeve or tube, and the base 504 and the light sources 612, 614, 616, 618 are received in a receptacle of the sleeve. In some embodiments, the cover 506 prevents the light sources 612, 614, 616, 618 from coming into contact with bodily fluids during and after implantation of the bone implant 500. In some embodiments, the cover 506 is transparent or clear. In other embodiments, the cover 506 is translucent. The light sources 612, 614, 616, 618 deliver light through the cover 506 to substantially all portions of the sidewall 124 of the bore 104 shallower than the head 502 of the rod 112.

Figure 7:
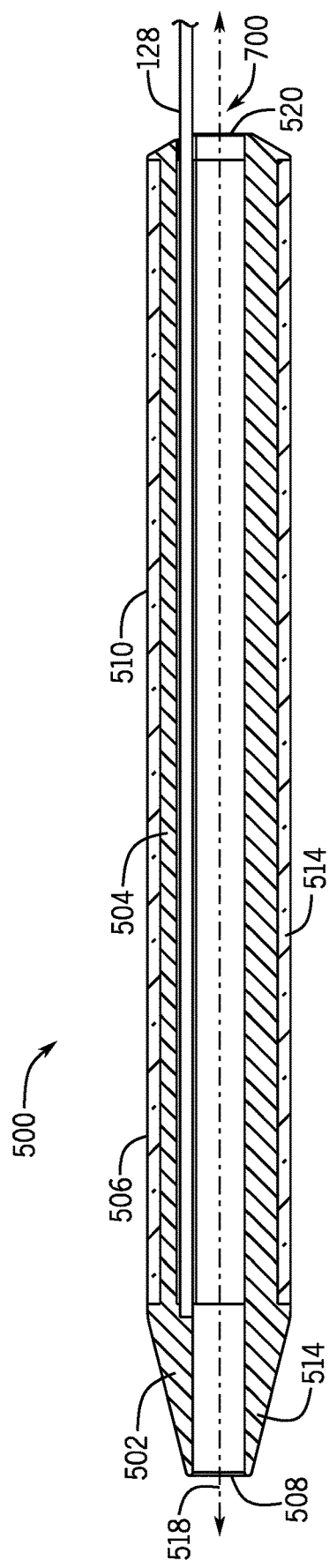
FIG. 7 is a cross-sectional view of the bone implant of FIGS. 5-6 along line 7-7 of FIG. 5.

FIG. 7 is a cross-sectional view of the bone implant 500 of FIGS. 5-6 taken along line 7-7 of FIG. 6. The bone implant 500 includes a bore or aperture 700 that extends entirely through the bone implant 500 along the central, longitudinal axis 518. Thus, the aperture 700 provides a continuous passage from the first end 508 to the second end 520 of the bone implant 500. As a result, the aperture 700 enables the bone implant 500 to be inserted into the bore 104 of the femur 102 via a guide wire. For example, a surgeon may employ a guide wire to drill or ream the bore 104 to a predetermined depth along the axis 108 extending through the center of the head 110 of the femur 102. Once the bore 104 is drilled or reamed, the surgeon may insert the guide wire into the aperture 700 of the bone implant 500 to direct the bone implant 500 into the bore 104 of the femur 102 via a path of the guide wire.

Figure 8:
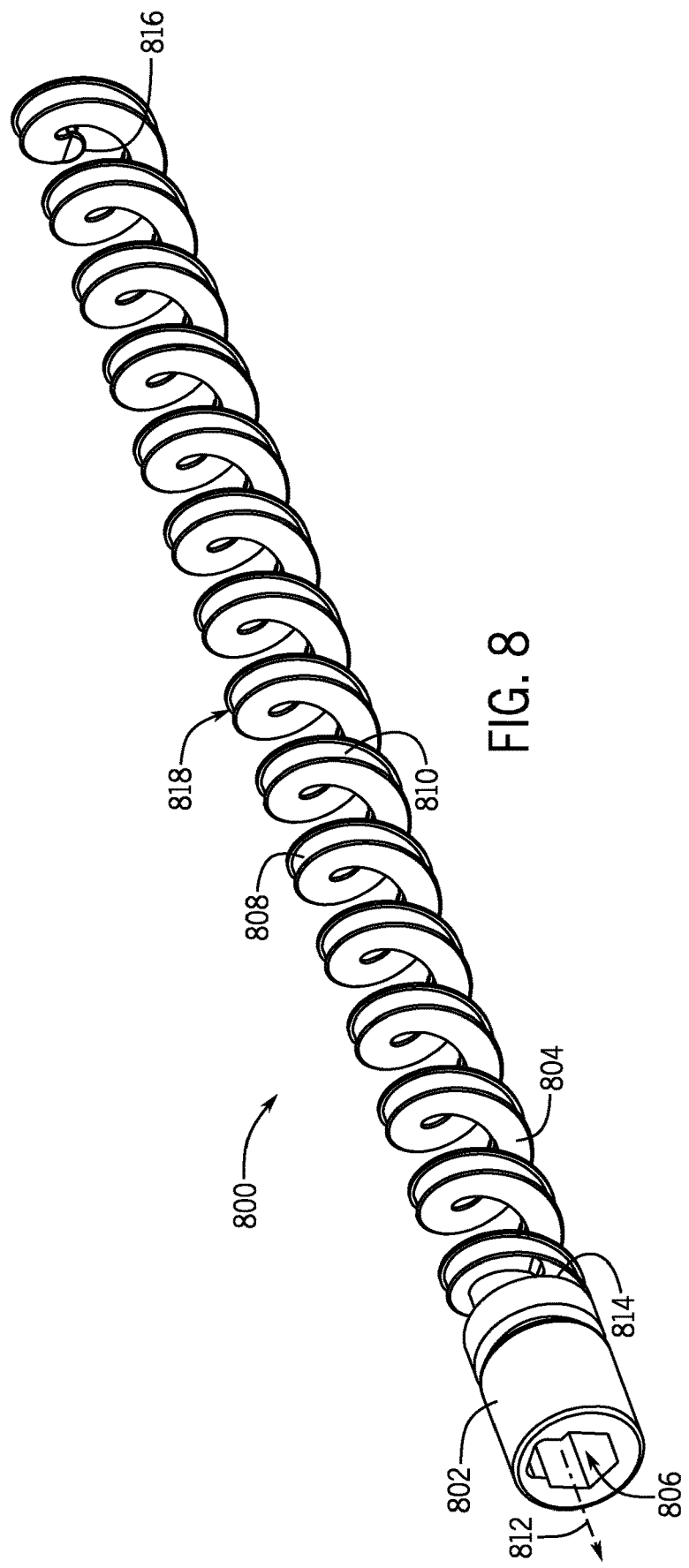
FIG. 8 is a perspective view of a bone implant according to yet another embodiment of the invention.

FIG. 8 is a perspective view of a bone implant 800 according to another embodiment of the invention. The bone implant 800 includes a head 802 and a coil 804. In some embodiments, the head 802 and the coil 804 are constructed of one or more inert materials such as, for example, 316L stainless steel, titanium, cobalt chrome, molybdenum alloy, and/or one or more additional and/or alternative materials. The head 802 of FIG. 8 is cylindrical and dimensioned to be received in the bore 104 of the femur 102 of FIG. 1. In other embodiments, the head 802 is other shapes such as rectangular, elliptical, etc. The head 802 of FIG. 8 includes a socket or receptacle 806 to receive a tool and/or a guide wire to facilitate insertion and/or implantation of the bone implant 800 into the bore 104 of the femur 102 of FIG. 1. In some embodiments, the first lead 128 and the second lead 130 extend into the socket 806 and operatively couple to the bone implant 800. When the bone implant 800 is implanted in the femur 102, the bone implant 800 is disposed entirely within the bore 104 and oriented so that the coil 804 is deeper in the bore 104 than the head 802.

In one embodiment, the bone implant 800 includes a first light source 808 disposed on an outer peripheral surface 810 of the coil 804. In some embodiments, the first light source 808 generates about 200 to about 250 mw/cm$^2$. The outer peripheral surface 810 is a surface of the coil 804 facing away from a central, longitudinal axis 812 of the coil 804. In one embodiment, the first light source 808 is an LED strip extending from a first or proximal end 814 to a second or distal end 816 of the coil 804. In some embodiments, the LED strip is an organic LED strip. In some embodiments, the LED strip is a thin, flexible strip having light emitting diodes connected in parallel. In some embodiments, the LED strip has a thickness of about two to three millimeters, a width of about six to ten millimeters, and a length substantially equal to a length of the coil 804 if straightened (e.g., 80-100 millimeters). However, the above-noted dimensions are merely examples and, thus, other dimensions may be used without departing from the scope of this disclosure. The first light source 808 is coiled about the bone implant 800. In some embodiments, the outer peripheral surface 810 of the coil 804 includes a first recess 818 in which the first light source 808 is seated.

Figure 9:
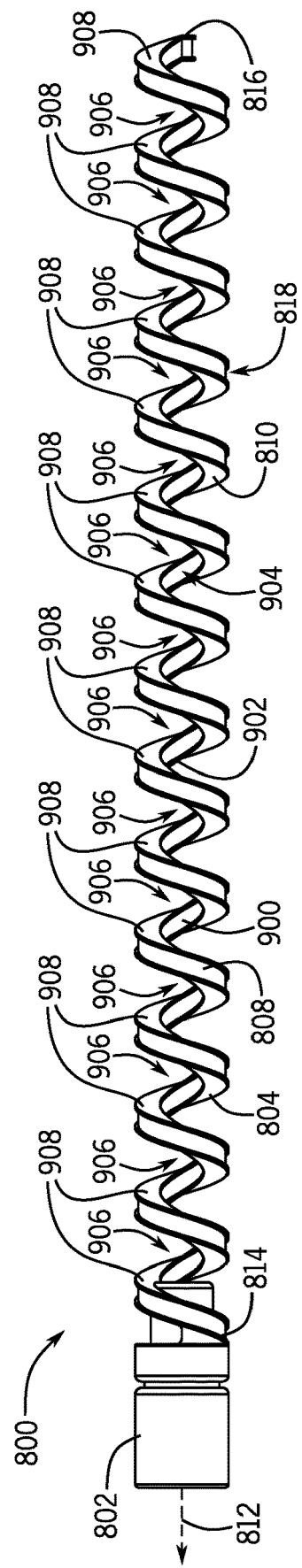
FIG. 9 is a side view of the bone implant of FIG. 8.

FIG. 9 is a side view of the bone implant 800 of FIG. 8. The bone implant 800 includes a second light source 900 disposed on an inner peripheral surface 902 of the coil 804. The second light source 900 is coiled about the bone implant 800. In some embodiments, the second light source 900 is substantially similar or identical to the first light source 808. The inner peripheral surface 902 is a surface of the coil 804 facing the central, longitudinal axis 812 of the coil 804. In some embodiments, the inner peripheral surface 902 includes a second recess 904 in which the second light source 900 is seated. In some embodiments, the first light source 808 and/or the second light source 900 are coupled to the coil 804 via a conductive adhesive such as paste or glue. In some embodiments, the first light source 808 and/or the second light source 900 are in contact with the coil 804 to facilitate heat transfer from the first light source 808 and/or the second light source 900 to the coil 804. Thus, the coil 804 can be a heat sink.

The first light source 808 and the second light source 900 are operatively coupled to the controller 126. The first light source 808 and the second light source 900 cooperate to deliver light to the femur 102. For example, the first light source 808 emits light away from the central, longitudinal axis 812 of the coil 804 to deliver the light to the sidewall 124 of the bore 104 of the femur 102. The second light source 900 emits light toward the central, longitudinal axis 812, and the light passes through spaces 906 between coils 908 of the coil 804 to deliver light to the sidewall 124 of the bore 104 of the femur 102.

In one embodiment, the first light source 808 and the second light source 900 emit near infrared (NIR) light (e.g., light having wavelengths from about 600 nanometers to about 950 nanometers). In some embodiments, the first light source 808 and the second light source 900 emit light having wavelengths of about 670 nanometers. In some embodiments, the light penetrates the femur 102 by about one-sixteenth of an inch, decreasing osteoblast apoptosis and promoting cell proliferation of the femur 102. In some embodiments, each of the first light source 808 and the second light source 900 has a viewing angle of about 120 degrees to about 170 degrees. In other embodiments, the first light source 808 and/or the second light source 900 has other viewing angles. Although the bone implant 800 of FIGS. 8-9 has two light sources, the bone implant 800 may include other numbers of light sources in other embodiments. For example, the bone implant 800 can include one light source, three light sources, five light sources, or other suitable numbers of individual or groups of light sources.

In some embodiments, the bone implant 800 includes a cover (not shown) such as PMMA overmolded to the coil 804 and the first light source 808 and the second light source 900. In some embodiments, the cover is a sleeve or tube, and the coil 804 and the first light source 808 and the second light source 900 are received in a receptacle of the sleeve. In some embodiments, the cover prevents the first light source 808 and the second light source 900 from coming into contact with bodily fluids during and after implantation of the bone implant 800. The cover can be transparent or clear. In other embodiments, the cover is translucent. The first light source 808 and the second light source 900 deliver light through the cover to substantially all portions of the sidewall 124 of the bore 104 deeper than the head 802 of the bone implant 800.

In some embodiments, the coil 804 secures the bone implant 800 to the femur 102 by expanding to apply force to the sidewall 124 of the bore 104 of the femur 102. For example, prior to implantation, the coil 804 can be contracted so that the coil 804 has a first outer diameter smaller than a diameter of the bore 104. Once the bone implant 800 is disposed in the bore 104, the coil 804 expands to contact the sidewall 124 and apply force to the sidewall 124 to secure the bone implant 800 to the femur 102.

Figure 10:
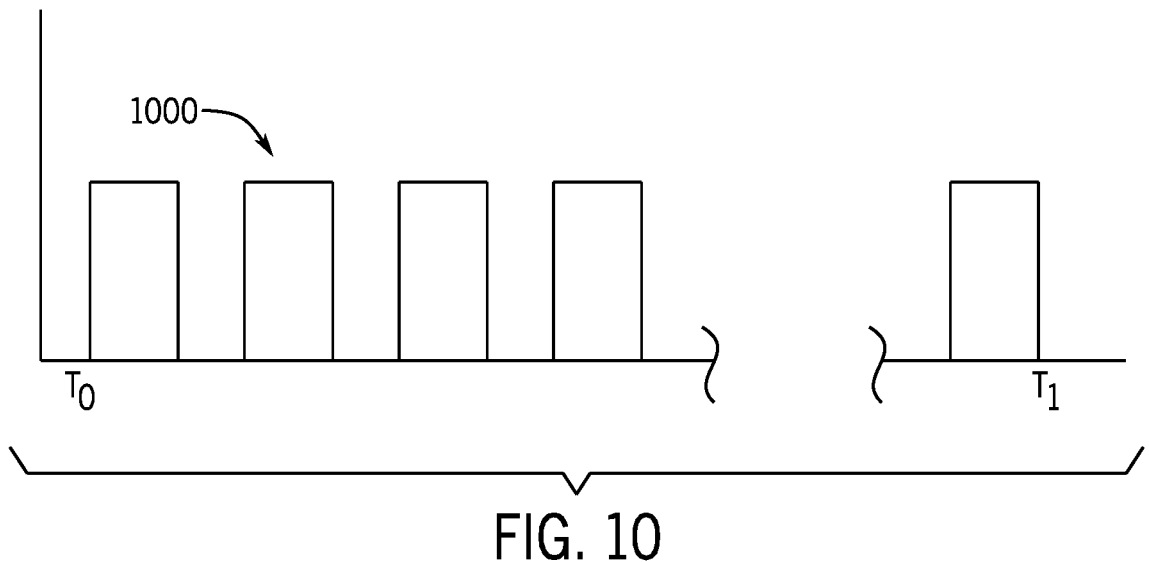
FIG. 10 is a graph of a waveform representative of power supplied to the bone implant of FIGS. 1-4, the bone implant of FIGS. 5-6, and/or the bone implant of FIGS. 7-8 to deliver a dose of light.

FIG. 10 is a graph illustrating a waveform 1000 representative of power supplied via the controller 126 of FIG. 1 to a bone implant such as, for example, the bone implant 100 of FIG. 1-4, the bone implant 500 of FIGS. 5-7, and/or the bone implant 800 of FIGS. 8-9 via the controller 126. The controller 126 employs pulse width modulation to control an amount of power supplied to the bone implant from a first time $T_0$ to a second time $T_1$ to control a dosage of light delivered by the bone implant to the femur 102. In some embodiments, the controller 126 controls the duty cycle of the power supplied to the bone implant to enable the bone implant to deliver a predetermined dosage of light to the femur 102. In one embodiment, the predetermined dosage of light is about four Joules of energy.

Figure 11:
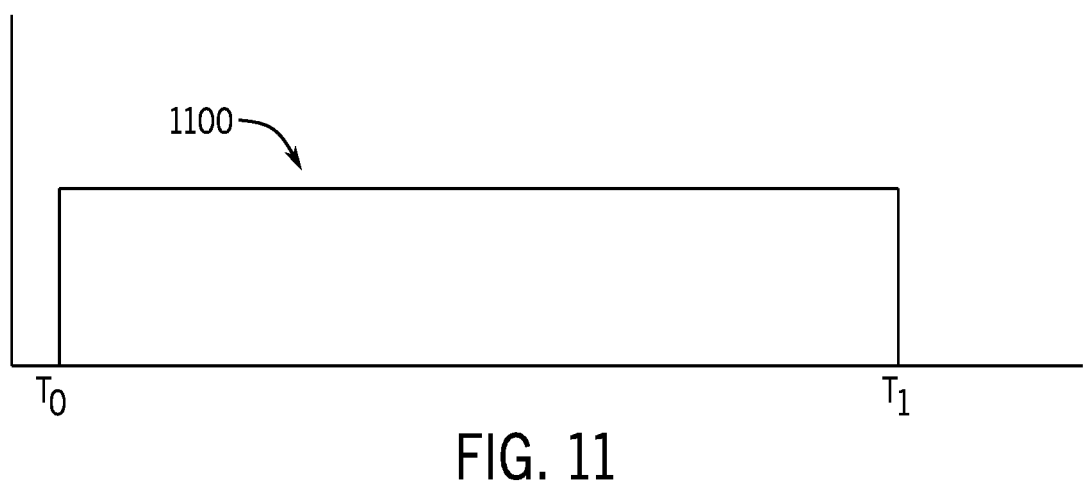
FIG. 11 is a graph of a waveform representative of power supplied to the bone implant of FIGS. 1-4, the bone implant of FIGS. 5-6, and/or the bone implant of FIGS. 7-8 to deliver a dose of light.

FIG. 11 is a graph illustrating a waveform 1100 representative of power supplied via the controller 126 of FIG. 1 to a bone implant such as, for example, the bone implant 100 of FIG. 1-4, the bone implant 500 of FIGS. 5-7, and/or the bone implant 800 of FIGS. 8-9. The controller 126 supplies power continuously to the bone implant from a first time $T_0$ to a second time $T_1$ so that the bone implant delivers a predetermined dosage of light to the femur 102. In one embodiment, the predetermined dosage of light is about four Joules of energy.

Figure 12:
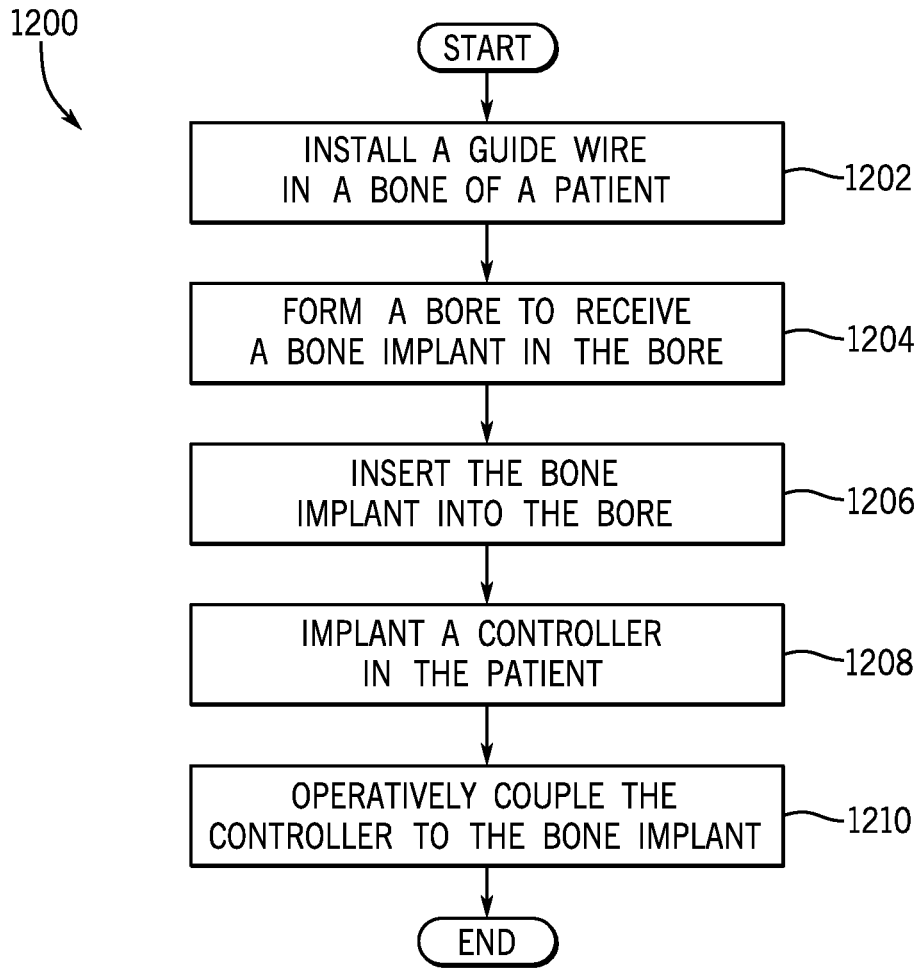
FIG. 12 is a flowchart of a method to implant the bone implant of FIGS. 1-4, the bone implant of FIGS. 5-6, and/or the bone implant of FIGS. 7-8 according to some embodiments of the invention.

FIG. 12 is a flowchart of a method 1200 to implant a bone implant such as, for example, the bone implant 100 of FIG. 1-4, the bone implant 500 of FIGS. 5-7, and/or the bone implant 800 of FIGS. 8-9. The method 1200 begins by installing a guide wire in a bone (e.g., the femur 102 of FIG. 1) of a patient (block 1202). For example, a surgeon can align an angle guide along an axis of a femoral shaft of the femur 102 to point a guide tube toward a center of the head 110 of the femur 102. The surgeon can drill a portion of a bore (e.g., the bore 104 of FIG. 1) to receive the bone implant. In some embodiments, the portion of the bore is a counter bore. In some embodiments, the surgeon confirms a position and/or path of a drill via an imaging device such as, for example, an X-ray machine. The surgeon inserts the guide wire into the portion of the bore. In some embodiments, the surgeon threads the guide wire to the femur 102 to secure the guide wire to the femur 102. In some embodiments, the surgeon confirms a position of the guide wire via an imaging device such as, for example, an X-ray machine.

If the guide wire is in a predetermined position, a measurement device can be slid over the guide wire to determine a depth of insertion of the guide wire. In some embodiments, another guide wire is installed in the femur 102, and a difference in length between the guide wires is determined to determine the depth of insertion of the guide wire initially installed.

The surgeon forms the bore to receive the bone implant (block 1204). In some embodiments, the surgeon drills and/or reams the bone to form the bore. In some embodiments, the surgeon drills and/or reams the bone to a depth greater than the depth of insertion of the guide wire such as, for example, a depth about five millimeters deeper than the depth of insertion of the guide wire.

The surgeon inserts the bone implant into the bore (block 1206). For example, the surgeon may position the bone implant within the bore so that the entire bone implant is disposed in the bore (e.g., flush or recessed relative the outer cortex 120). In some embodiments, the bone implant is inserted into the bore along a path of the guide wire. For example, the bone implant can include an aperture (e.g., the aperture 314 of FIG. 3, the aperture 700 of FIG. 7, through the coils 908 and the receptacle 806 of FIG. 9), and the surgeon can insert the guide wire into the aperture to direct the bone implant into the bore via the path of the guide wire.

The surgeon implants a controller (e.g., the controller 126 of FIG. 1) into the patient (block 1208). In some embodiments, the surgeon implants the controller in subcutaneous tissue of the patient. In other embodiments, the surgeon implants the controller in other locations within the patient. In other embodiments, the controller is disposed outside of the patient and, thus, the surgeon does not implant the controller in the patient.

The surgeon operatively couples the controller to the bone implant (block 1210). In some embodiments, the surgeon operatively couples the controller to the bone implant via leads (e.g., the first lead 128 and the second lead 130). For example, the surgeon can form one or more tunnels through the subcutaneous tissue from the bone implant to the controller, guide the leads through the tunnel(s), and connect the leads to the controller. In some embodiments, the surgeon tests an integrity of a circuit formed via the leads. In embodiments in which the controller is disposed outside of the patient, the surgeon can pass the leads through a subcutaneous tunnel and through skin of the patient to connect the leads to the controller. Once the bone implant is operatively coupled to the controller, the surgeon closes all incisions.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

The invention claimed is:

1. A bone implant to be implanted inside a bone of a patient, the bone implant comprising:
a base having an aperture extending entirely through the base, the aperture defining an interior surface of the base; and
a light source coupled to the base at a position radially outward, away from the interior surface of the base, the light source to emit light onto bone adjacent the bone implant to at least one of stimulate bone growth or reduce bone loss,
the bone implant, including the base and the light source, configured to be implanted inside the bone of the patient,
the light source having a length that is substantially similar to the length of the base, and
the light source being configured to emit light radially away from a longitudinal axis of the base.

2. The bone implant of claim 1, and further comprising a spline and a flute, the light source disposed on the flute.

3. The bone implant of claim 2, and further comprising a transparent cover surrounding the spline and the light source.

4. The bone implant of claim 1, and further comprising a coil.

5. The bone implant of claim 1, wherein the light source comprises a light emitting diode disposed on the coil.

6. The bone implant of claim 1, and further comprising a head having a pointed, distal end.

7. The bone implant of claim 1, and further comprising a head and a rod extending from the head.

8. The bone implant of claim 7, wherein the head includes threads.

9. The bone implant of claim 1, wherein the light source includes a light emitting diode strip having a plurality of light emitting diodes.

10. The bone implant of claim 1, further comprising:
a second light source; and
a third light source;
wherein the first light source, the second light source, and the third light source extend substantially parallel to the longitudinal axis of the base.

11. A bone implant to be implanted inside a bone of a patient, the bone implant, comprising:
a base having a longitudinal axis, an exterior surface, and an aperture extending along the longitudinal axis through the base, the aperture defining an interior surface of the base; and
a light source coupled to the exterior surface of the base, and
the bone implant, including the base and the light source, configured to be implanted inside the bone of the patient,
the light source having a length that is substantially similar to the length of the base, and
the light source being configured to emit light radially away from a longitudinal axis of the base.

12. The bone implant of claim 11, further comprising a controller operatively coupled to the light sources, the controller to control a dosage of light emitted via the light sources.

13. The bone implant of claim 12, wherein the dosage of light is four Joules to six Joules of energy per day.

14. The bone implant of claim 11, further comprising a cover covering the light sources and a portion of the rod, wherein the cover is transparent.

15. The bone implant of claim 11, wherein each of the light sources is to generate radiant power exposure of about 200 milliwatts per square centimeter to about 250 milliwatts per square centimeter.

16. The bone implant of claim 11, wherein the light source includes a light emitting diode strip having a plurality of light emitting diodes.

17. The bone implant of claim 11, wherein the light source emitting light has wavelengths from about 600 nanometers to about 950 nanometer.

18. A bone implant to be implanted inside a bone of a patient, the bone implant receiving a guidewire, the bone implant comprising:
- a base having an aperture extending entirely through the base, the aperture defining an interior surface of the base, the aperture of the base including a continuous passage from a first end of the base to a second end of the base to receive the guidewire; and
- a light source coupled to the base at a position radially outward, away from the interior surface of the base, the light source to emit light onto bone adjacent the bone implant to at least one of stimulate bone growth or reduce bone loss, and
- the bone implant, including the base and the light source, configured to be implanted inside the bone of the patient.

19. The bone implant of claim 18, wherein the light source has a length that is substantially similar to the length of the base, and
- wherein the light source is configured to emit light radially away from a longitudinal axis of the base.

20. The bone implant of claim 18, further comprising:
- a battery;
- a temperature sensor;
- a controller in electrical communication with the light source, the battery, and the temperature sensor, the controller being configured to:
  - power the light source so the light source emits light for a predetermined amount of time;
  - receive temperature information from the temperature sensor; and
  - based on the temperature information exceeding a temperature threshold, stop supplying power from the battery to the bone implant.

* * * * *